(12) United States Patent
Huynh et al.

(10) Patent No.: US 6,261,130 B1
(45) Date of Patent: Jul. 17, 2001

(54) HIGH-DENSITY POGO PIN CONNECTOR

(75) Inventors: Ky Huynh, Tigard; Larry L. Davis, Milwaukie, both of OR (US)

(73) Assignee: MHL Development Company, Inc., Portland, OR (US)

( * ) Notice: Subject to any disclaimer, the term of this patent is extended or adjusted under 35 U.S.C. 154(b) by 0 days.

(21) Appl. No.: 09/488,223

(22) Filed: Jan. 19, 2000

(51) Int. Cl.[7] .................................................. H01R 13/24
(52) U.S. Cl. ............................................. 439/700; 439/824
(58) Field of Search ................................... 439/700, 824, 439/289

(56) References Cited

U.S. PATENT DOCUMENTS

| | | |
|---|---|---|
| 3,363,220 * | 1/1968 | Redd et al. ........................... 439/700 |
| 3,422,387 * | 1/1969 | Sprigings et al. ................... 439/700 |
| 3,431,428 * | 3/1969 | Valer .................................... 439/700 |
| 4,734,050 | 3/1988 | Negre et al. . |
| 4,904,213 | 2/1990 | Hock et al. . |
| 5,133,680 | 7/1992 | Watson et al. . |
| 5,417,595 * | 5/1995 | Cullen et al. ........................ 439/700 |
| 5,509,813 | 4/1996 | Lu . |
| 5,594,356 | 1/1997 | Turner et al. . |
| 5,641,315 | 6/1997 | Swart et al. . |
| 5,749,754 | 5/1998 | Patterson et al. . |
| 5,762,504 | 6/1998 | Itoh . |
| 5,813,876 | 9/1998 | Rutigliano . |
| 5,857,866 | 1/1999 | Felps . |

* cited by examiner

*Primary Examiner*—Khiem Nguyen
*Assistant Examiner*—Hae Moon Hyeon
(74) *Attorney, Agent, or Firm*—Timothy E. Siegel

(57) ABSTRACT

A high pin count electrical connector assembly for electrically connecting a set of first conductors to a set of second conductors according to a predetermined connective scheme. The connector assembly includes a male-half connector that has an array of spring-loaded pins, each of which is connected to a separate first conductor, and further has a male half connective bracket. A female-half connector has an array of contact regions positioned in matching arrangement to the array of spring-loaded pins, and each connected to a separate second conductor, and further has a female-half connective bracket configured to releasably mate with said male-half connective bracket so that when said male-half bracket and said female-half bracket are correctly mated together said spring loaded pins are held in contact with said contact regions so that said first conductors and said second conductors are electrically connected according to said predetermined scheme.

5 Claims, 4 Drawing Sheets

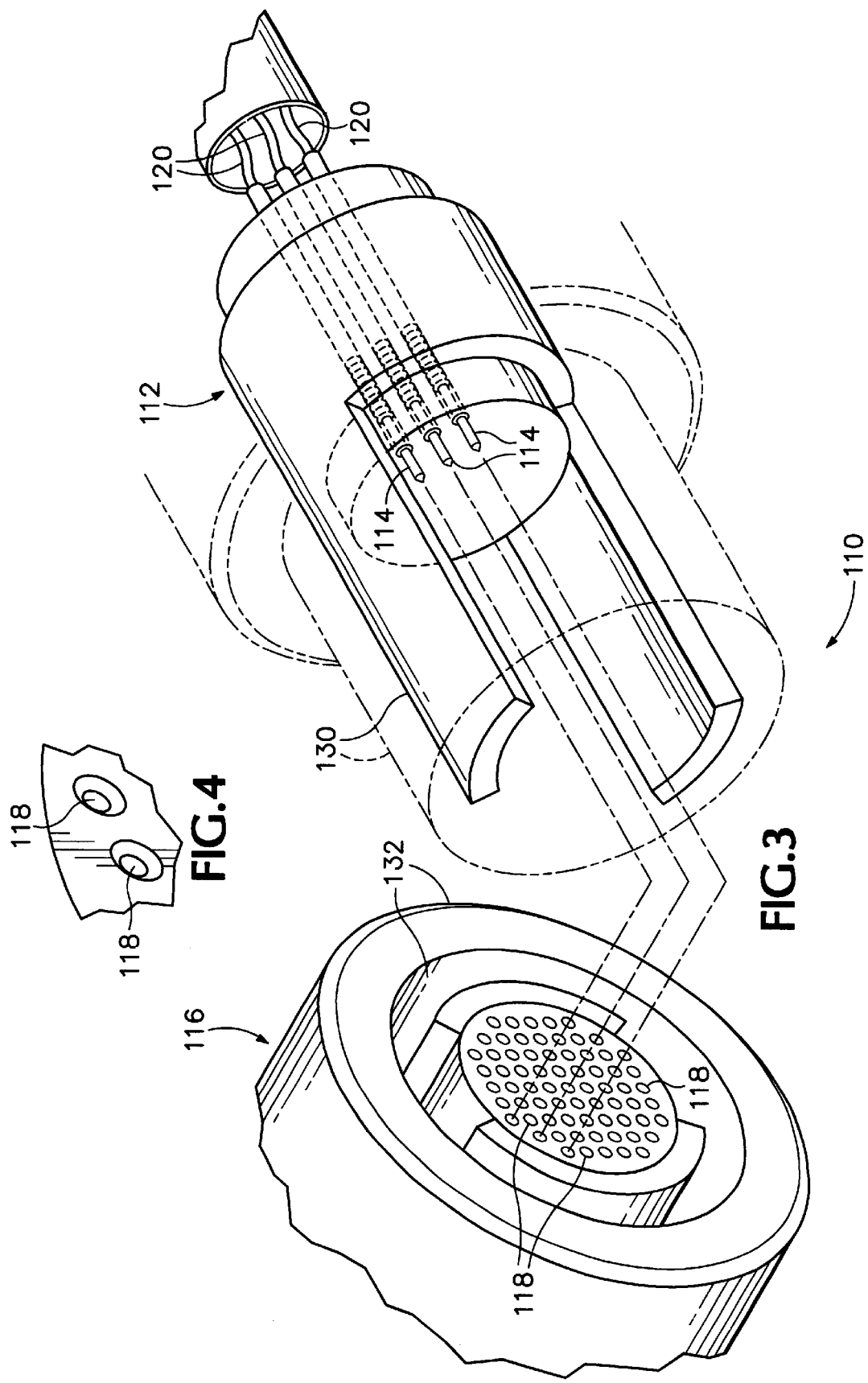

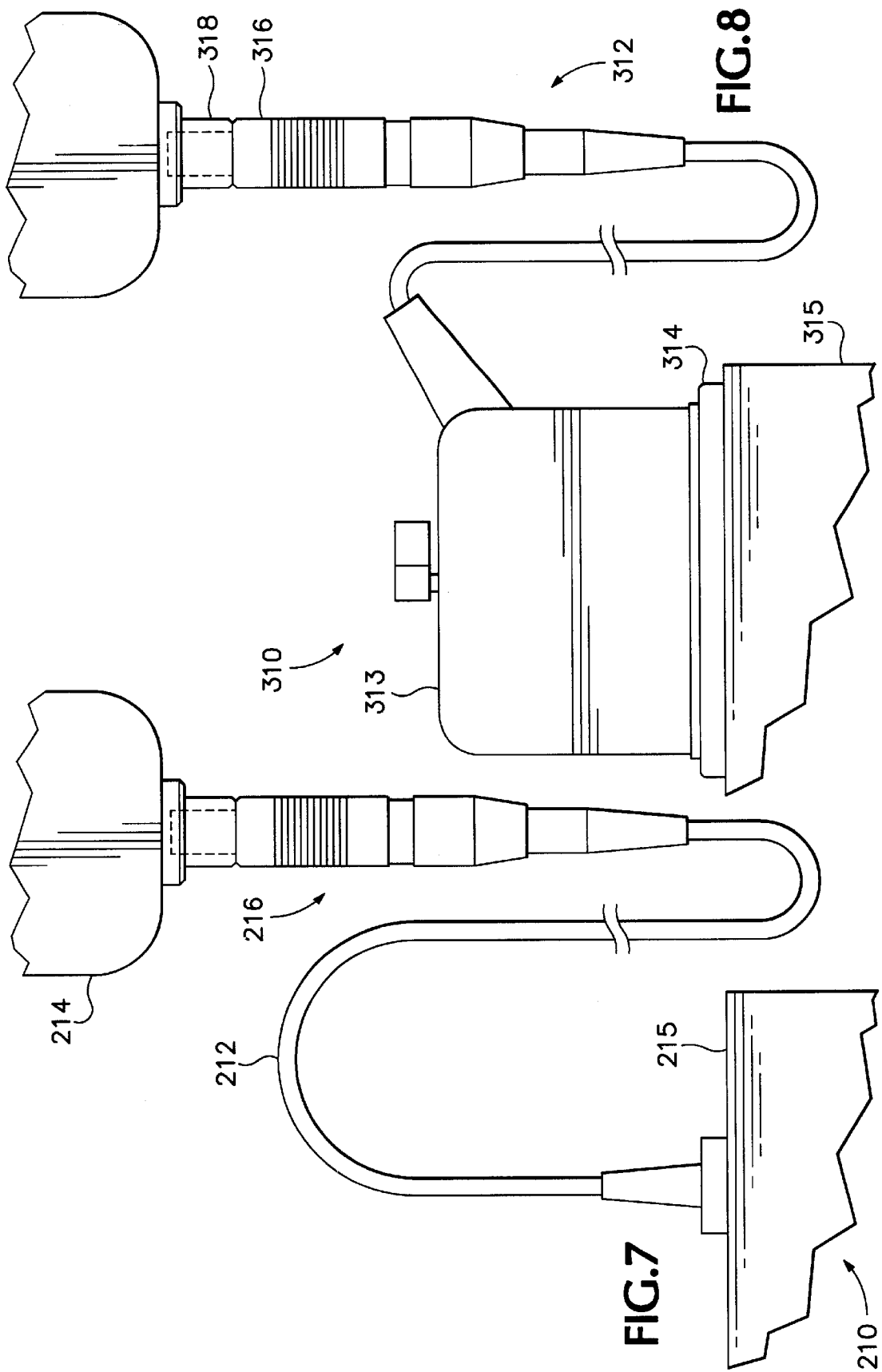

HIGH-DENSITY POGO PIN CONNECTOR

BACKGROUND OF THE INVENTION

The present invention is a high-density pogo pin connector and a data gathering and analysis station making use of the same.

The manner in which electrical connectors are presently configured places an upper limit on the number of pins that may be connected over a given connector face surface area. This limitation on pin density results in a bulky construction for high pin count (ie, greater than 20 pins) connector designs. FIG. 1 shows a pin-to-pin socket structure that is typical for a prior art connector. The pin socket 2 includes one contact 4, in the general form of a leaf spring that touches the side of the mating pin 6. Accordingly, the pin 6 must which must fit snugly in pin socket 2 to ensure that contact 4 touches pin 6 when the connector halves are engaged. The need for a snug fit in turn creates a requirement that each pin 4 be positioned relative to its neighboring pins such that every pin precisely match in position the location of a pin socket. If one pin is misplaced or bent slightly, the entire connector will not mate and will not be usable. This requirement imposes a burdensome manufacturing task that tends to become impractical, and results in poor performance, for a pin density above about 10 per cm².

The bulky construction of high pin count electrical connectors in turn forces an awkward and expensive configuration for some devices that make use of high pin count electrical connectors. For example, ultrasound-monitoring stations frequently come equipped with a number of specialized probes for performing different ultrasound scanning functions. As shown in FIG. 1 each probe 10 is fixedly attached to a cable 12 that bears a connector 14 for connecting to a mating connector 16 on the ultrasound monitoring station data analysis and display unit 18. This configuration is necessitated by the bulky nature of the cable connector pair 14 and 16. If the connector were located on the probe end of the cable, the probe would be rendered bulky and difficult to manipulate. Unfortunately, this configuration is expensive because it means that a separate cable must be provided for each one of the ultrasound probes. As each one of these cables costs on the order of $1000, this adds considerable expense to the ultrasound monitoring station. Moreover, because the lack of a sufficiently high pin density connector forces each ultrasound probe to be manufactured and sold bundled with a cable, as a single unit, a problem with either the probe or the cable necessitates the replacement of the entire probe/cable unit. Accordingly, a probe/cable unit must be replaced when the probe has been damaged, even if the cable portion is still fully operative and vice versa.

SUMMARY

In a first separate aspect, the present invention is a high pin count electrical connector assembly for electrically connecting a set of first conductors to a set of second conductors according to a predetermined connective scheme. The connector assembly includes a male-half connector that has an array of spring-loaded pins, each of which is connected to a separate first conductor, and also has a male half connective bracket. A female-half connector has an array of contact regions positioned in matching arrangement to the array of spring-loaded pins, each of which connects to a separate second conductor, and also has a female-half connective bracket configured to releasably mate with the male-half connective bracket. Therefore, when the male-half bracket and the female-half bracket are correctly mated together the spring loaded pins are held in contact with the contact regions so that the first conductors and the second conductors are electrically connected according to determined scheme.

In a second separate aspect the present invention is a data gathering and analysis station including. A probe of the station has a multiplicity of separate receive elements and is adapted to be manipulated by a human hand. Further, a multi-conductor electrical cable is releasably connected to the probe, and is adapted to transmit information from the receive elements of the probe. In addition, a data analysis and display unit is connected to the cable and is adapted to receive the information from the cable. Finally, the multi-conductor electric cable and the probe are releasably connected together by an electrical connector having a mating pair of connective elements for each of the separate receive elements in the probe, arranged at a density of greater than 10 per cm².

In a third separate aspect the present invention is a cable assembly adapted to permit the retrofitting of a data gathering and analysis station and comprising a cable having a first end and a second end. In addition, a low pin density connector is electrically and physically connected to the first end of the cable and a high pin density connector is electrically and physically connected to the second end of the cable.

In a fourth separate aspect the present invention is a data-gathering probe comprising a set of data-gathering elements. Additionally, a high pin density connector has a set of contact elements, each of which is connected to a data-gathering element by a conductive element.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 3 is a perspective view of a connector according to the present invention.

FIG. 4 is an expanded perspective view of two indented contact regions of the connector of FIG. 3.

FIG. 7 is a plan view of an ultrasound station probe cable and connector assembly according to the present invention.

FIG. 8 is a plan view of a retrofitted ultrasound probe cable and connector assembly according to the present invention.

DETAILED DESCRIPTION OF THE PREFERRED EMBODIMENT

Figure 1:
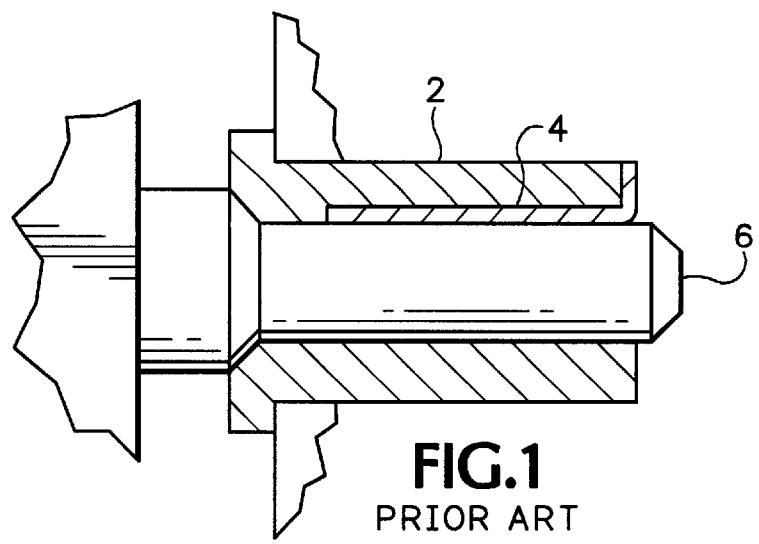
FIG. 1 is an expanded cross-sectional view of a prior art pin-to-pin socket connection.
Figure 2:
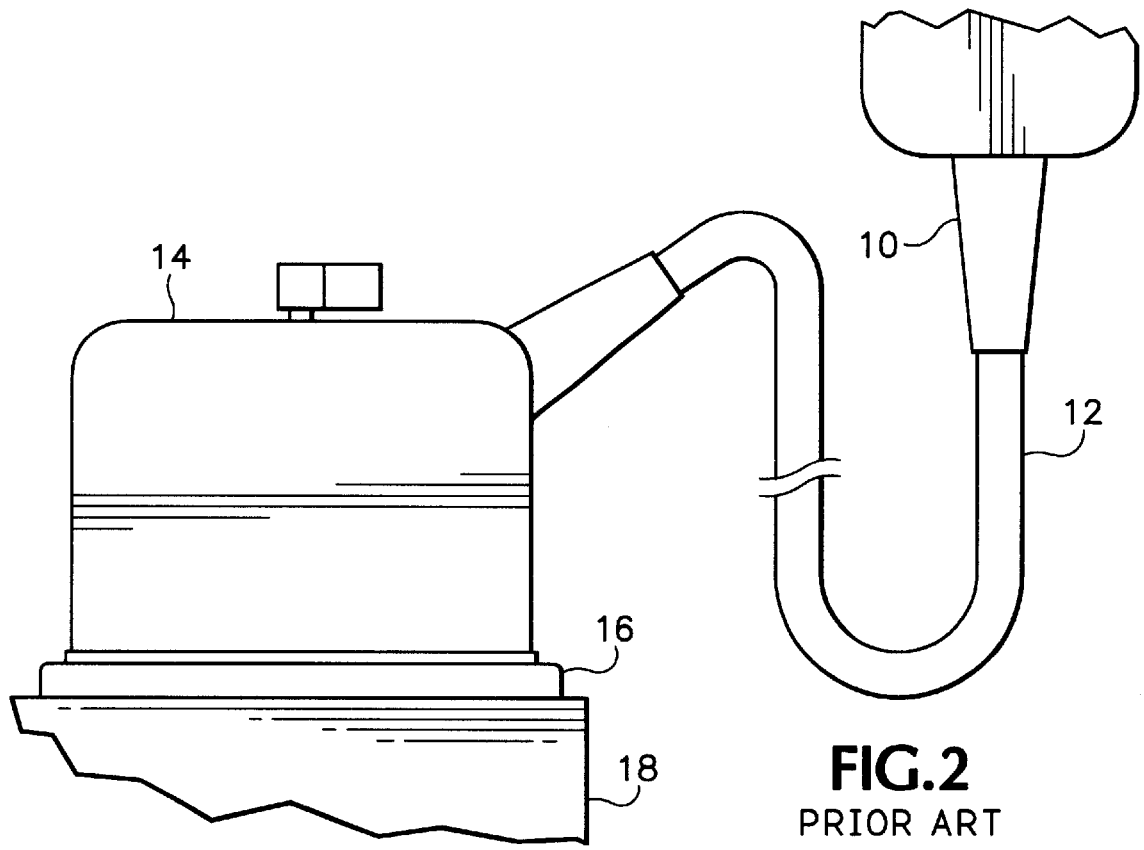
FIG. 2 is a plan view of a prior art ultrasound station probe cable and connector assembly.

Referring to FIGS. 3 and 4 a preferred embodiment of a high pin density electrical connector assembly 110 according to the present invention includes a male-half connector 112 having a set of pogo, or "spring loaded" pins 114, three of which are shown in FIG. 3. A female-half connector 116 is configured to mate with male-half, and has an array of contact regions 118. Pogo pins 114 and contact regions 118 are arrayed in a matching pattern so that when the male-half connector 112 and the female-half connector 116 are mated, each pogo pin contacts a corresponding connective region 118. Each pogo pin 114 is connected to a conductor 120, such as a conductive wire, as is every conductive region.

A male-half bracket 130 and a female-half bracket 132 releasably bond together by way of structures and techniques that are well known in the industry, to maintain pogo pins 114 in contact with contact regions 118. A pair of guide indicators (not shown) may be provided on the exterior of brackets 130 and 132 to aid personnel in correctly aligning pins 114 and contact regions 118. Referring to FIG. 4, in one preferred embodiment, contact regions 118 are indented as shown so that they urge each pogo pin 114 into the center of its corresponding contact region 118, resulting in a more robust set of contacts. In one preferred embodiment, sixty-four pins 114 are arranged over a surface area of approximately 1 cm$^2$.

Figure 5:
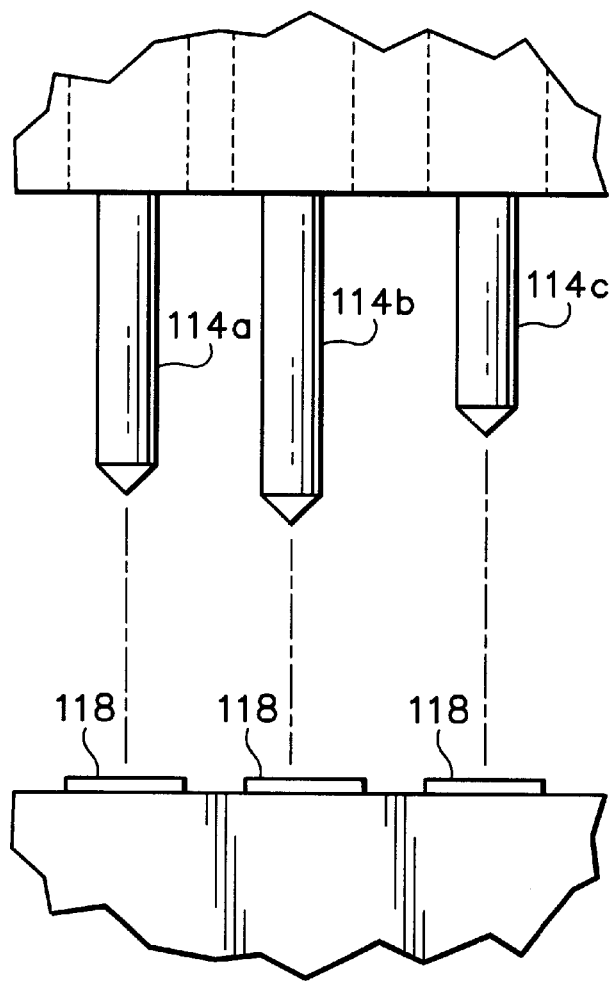
FIG. 5 is a greatly expanded side view of some pins and contact regions of the connector of FIG. 3, with the misalignment of the pins exaggerated for purposes of clarity.
Figure 6:
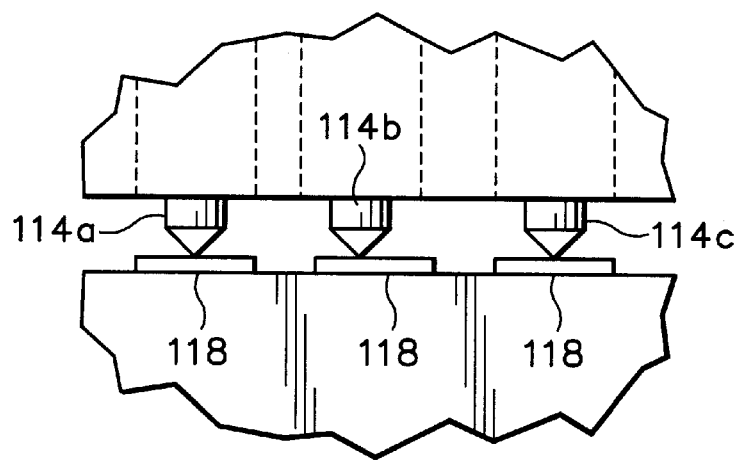
FIG. 6 is a greatly expanded view of the pins and contact regions of FIG. 5 after they have been brought into mutual contact.

Referring to FIGS. 5 and 6, the advantages of this configuration should now be apparent. Receptive regions 118, unlike the pin sockets of prior art connectors, can be considerably wider than pins 114 without jeopardizing the formation of a robust contact. As a result, pins 114 (and more particularly the tips of pins 114, pins 114, which may be termed "pin contact regions") do not need to be positioned relative to one another and to bracket 130 with the same level of accuracy as pins that mate with openings in accordance with the prior art. FIGS. 5 and 6 show an example of this, with pins 114a and 114b placed much closer together than pins 114b and 114c. As FIG. 5 shows, a full set of contacts are formed nevertheless. Because pins 114 are spring loaded, differences in the degree to which they protrude outwardly from the rest of male-half 112 are forgiven upon contact with regions 118. This phenomenon is also shown in FIGS. 5 and 6, with FIG. 5 showing pins 114a and 114b protruding farther than pin 114c. FIG. 6 shows that contact pads 118 push all the pins 114 back so that a contact is formed with each pin 114. If pins 114 were not spring loaded, pins 114a and 114b would prevent pin 114c from making contact.

The relaxation of the requirement for accuracy in pin placement permits the construction of a connector 110 with a greatly increased pin density. As a result, an electrical cable having a particular number of separate conductors that are mutually insulated from one another may be releasably connected to a mating electrical device with a connector that is much smaller and lighter than was heretofore possible.

Referring to FIG. 7, a preferred embodiment of a separate aspect of the invention is a data gathering and analysis station 210, which would most typically be an ultrasound imaging station, having a multiconductor cable 212, that connects a data-gathering probe 214 (typically an ultrasound transceiver probe) to a data analysis and display unit 215. Cable 212 is releasably connected to probe 214 by way of a high pin density connector assembly 216. Connector assembly 216 is most typically the same as connector 110 in the details of its construction. Probe 214 is typically one of several probes associated with station 210, each such probe being specially adapted for a particular type of data collection. For example, many ultrasound stations have several different probes, each specialized for imaging from a different vantage point on or in the human body. As noted in the BACKGROUND OF THE INVENTION section, in the prior art a separate probe/cable assembly was required for each one of these functions, driving up the overall cost of the ultrasound imaging station. With the present invention it is now possible to connect each one of several probes to the ultrasound imaging station using a single cable only, thereby greatly saving on the expense of outfitting the imaging station.

Referring to FIG. 8, an ultrasound imaging station 310 has been retrofitted with a cable assembly 312 having a prior art standard connector 313 for connecting to a mating connector 314 of a prior art data analysis and display unit 315. The opposite end of cable assembly 312 is fitted with a high pin density connector 316, for connecting to an ultrasound probe assembly fitted with a mating connector 318. Accordingly, cable assembly 312, when installed onto a prior art data analysis and display unit 315 renders unit 315 capable of connecting to probes having high pin density connector 318. In one preferred variant, connector 316 is the same as male connector 112 and connector 318 is the same as female connector 116. In a separate preferred variant, connector 316 is the same as female connector 116 and connector 318 is the same as male connector 112.

The spring loaded, or pogo, pins are available as 0.010–0.015 centers Penta O Spring Contact Probes, from Penta at telephone No. 913-342-5544.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A high pin count electrical connector assembly for electrically connecting a set of first conductors to a set of second conductors according to a predetermined connective scheme, and comprising:

a) a male-half connector having an array of spring-loaded pins, each said pin being connected to a separate first conductor and defining a pin contact region at its distal tip, and further having a male half connective bracket;

b) a female-half connector having an array of receptive contact regions positioned in matching arrangement to said array of spring-loaded pins and each being at least twice the area of the corresponding pin contact region, and each connected to a separate second conductor, and further having a female-half connective bracket configured to releasably mate with said male-half connective bracket so that when said male-half bracket and said female-half bracket are correctly mated together said spring loaded pins are held in contact with said contact regions so that said first conductors and said second conductors are electrically connected according to said predetermined scheme.

2. The electrical cable connector of claim 1 in which said first conductors are bound together into an electrical cable.

3. The electrical cable connector of claim 1 in which said second conductors are bound together into an electric cable.

4. The electrical cable connector of claim 1 in which said spring loaded pins are concentrated together with a density of greater than 10 per cm$^2$.

5. The electrical cable connector of claim 1 in which said contact regions are indented for urging said male pins into a robust set of contacts with said contact regions.

* * * * *